United States Patent [19]

Winn

[11] 4,029,665

[45] June 14, 1977

[54] 8-ARALKYL-1,4-ETHANO-5H-[1]BENZOPYRANO[3,4-B]PYRIDINES

[75] Inventor: Martin Winn, Deerfield, Ill.

[73] Assignee: Abbott Laboratories, North Chicago, Ill.

[22] Filed: Mar. 7, 1975

[21] Appl. No.: 556,238

Related U.S. Application Data

[63] Continuation-in-part of Ser. No. 345,943, April 2, 1973, abandoned.

[52] U.S. Cl. .................. 260/293.53; 424/267; 260/293.55
[51] Int. Cl.² .................. C07D 405/14
[58] Field of Search ............. 260/293.53, 293.55

[56] References Cited

UNITED STATES PATENTS

| | | | |
|---|---|---|---|
| 3,514,464 | 5/1970 | Pars et al. | 260/295 |
| 3,535,327 | 10/1970 | Pars et al. | 260/295 |
| 3,656,906 | 4/1972 | Bullock | 23/230 B |
| 3,661,919 | 5/1972 | Razdan et al. | 260/297 R |
| 3,728,360 | 4/1973 | Pars et al. | 260/345.3 |
| 3,787,424 | 1/1974 | Pars et al. | 260/295 T |
| 3,905,969 | 9/1975 | Harris et al. | 260/247.2 B |

Primary Examiner—John M. Ford

Attorney, Agent, or Firm—Vincent A. Mallare; Robert L. Niblack

[57] ABSTRACT

A new series of 8-aralkyl-1,4-ethano-5H-[1]benzopyrano[3,4-b]pyridines having anti-convulsant activity, and compounds useful in the preparation thereof. The compounds are represented by the formula

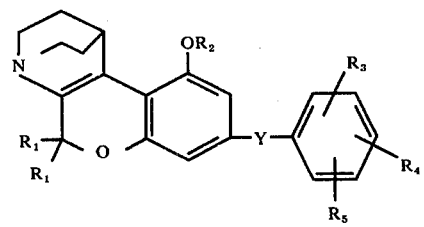

wherein each $R_1$ is loweralkyl; $R_2$ is hydrogen, loweralkyl, loweracyl and substituted acyl; Y is a straight or branched chain alkylene group having from one to ten carbon atoms and each $R_3$, $R_4$ and $R_5$ are the same or different members of the group consisting of hydrogen, halo, trifluoromethyl, or loweralkyl; and the pharmaceutically acceptable salts thereof.

4 Claims, No Drawings

8-ARALKYL-1,4-ETHANO-5H-[1]BEN-ZOPYRANO[3,4-B]PYRIDINES

CROSS-REFERENCE TO RELATED APPLICATIONS

This application is a continuation-in-part of co-pending application Ser. No. 345,943 filed on Apr. 2, 1973, now abandoned.

DETAILED DESCRIPTION OF THE INVENTION

This invention relates to a new series of 8-aralkyl-1,4-ethano-5H[1]benzopyrano[3,4-b]pyridines, to intermediates useful in the preparation thereof, and to methods of preparing and using the compounds.

The compounds of this invention are represented by formula I

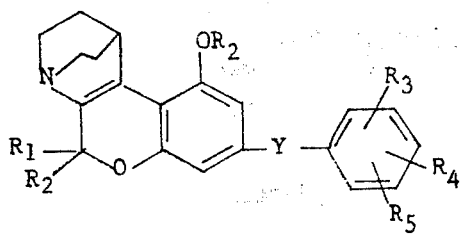

wherein each $R_1$ is loweralkyl; $R_2$ is hydrogen, loweralkyl, loweracyl and substituted acyl; Y is a straight or branched chain alkylene group having from one to ten carbon atoms and each $R_1$, $R_2$ and $R_3$ are the same or different members of the group consisting of hydrogen, halo, trifluoromethyl, loweralkyl; and the pharmaceutically acceptable salts thereof.

As used herein, the term "loweralkyl" means saturated monovalent, aliphatic radicals, including straight or branched chain radicals of from one to six carbon atoms, as illustrated by, but not limited to methyl, ethyl, propyl, isopropyl, butyl, sec-butyl, amyl, hexyl, and the like.

The term "halo" includes chloro, fluoro, bromo and iodo.

The term "pharmaceutically acceptable acid addition salts" refers to salts prepared by reacting the amine with an organic or inorganic acid. Representative salts include hydrochloride, hydrobromide, sulfate, bisulfate, acetate, valerate, oleate, laurate, borate, benzoate, lactate, phosphate, tosylate, citrate, maleate, succinate, tartrate, napsylate and the like.

The intermediates of this invention are represented by formula II

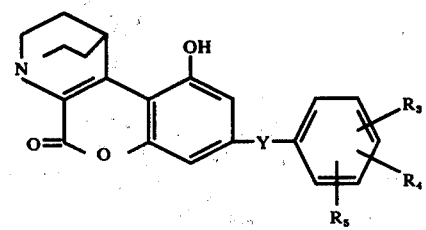

Generally speaking, the compounds of Formula I are prepared by reacting a compound of Formula II with a loweralkyl magnesium halide as illustrated by the equation:

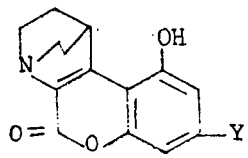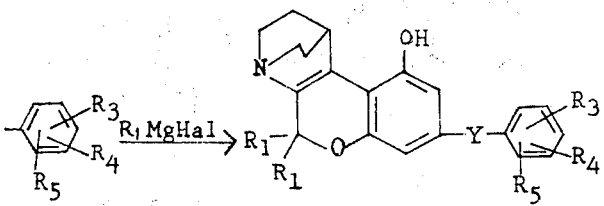

wherein $R_1$, $R_3$, $R_4$ and $R_5$ have the meanings given above, and Hal represents halogen. The reaction is carried out in an organic solvent under the conditions of the reaction, for example, diethyl ether, dibutyl ether, tetrahydrofuran, anisole, pyridine and the like. It is preferred to add a solution of the 8-aralkyl-1,4e-thano-10-hydroxy-5-oxo-1,2,3,4-tetrahydro-5H-[1]benzopyrano[3,4-b]pyridine in a pyridine or anisole solution, or in a mixture of these solvents, to solution of the Grignard reagent in anisole.

The intermediates of Formula II are prepared by reacting a loweralkyl-3-quinuclidinone-2-carboxylate of Formula III with a 5-aralkylresorcinol of Formula IV. The reaction can be carried out in a mixture of concentrated sulfuric acid and phosphorous oxychloride, or, preferably, in a mixture of methanesulfonic acid and phosphorus oxychloride, and is represented by the following reaction scheme:

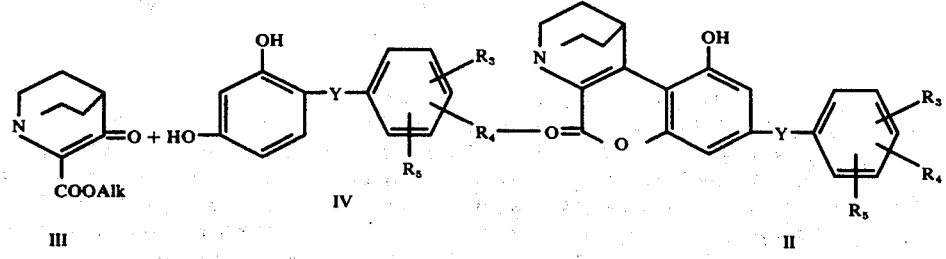

The loweralkyl 3-quinuclidinone-2-carboxylates of Formula III are known in the art.

The 5-aralkyl resorcinols are prepared by processes analogous to those known in the art for the preparation of 5-alkyl resorcinols, by, for example, the methods illustrated by the following reaction schemes:

Preferred synthetic routes are represented by the following reaction schemes:

The specificity of action of the 8-aralkyl compounds makes them more valuable pharmacological agents than are the corresponding 8-alkyl compounds of the prior art.

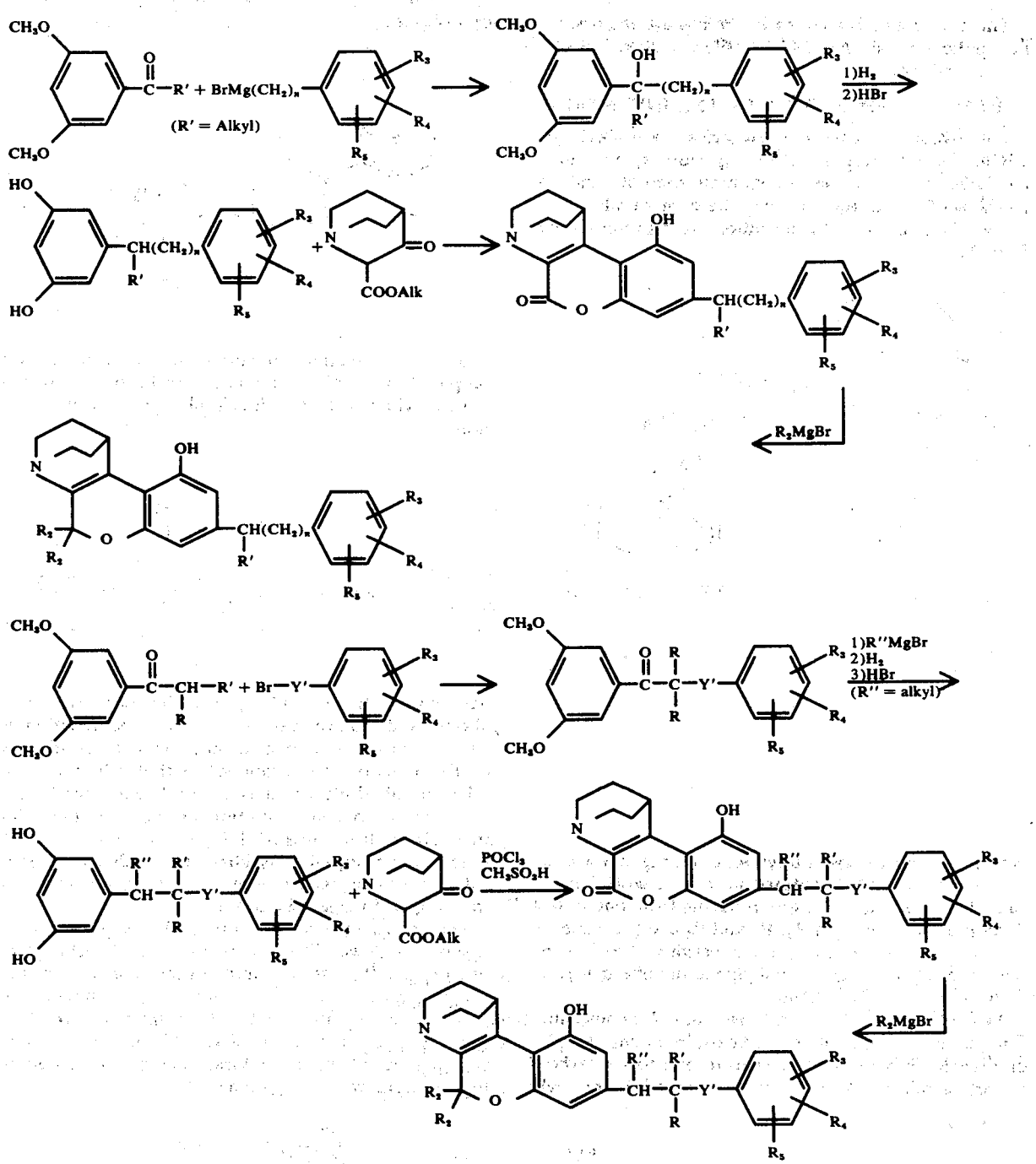

The compounds of formula I have been shown to possess anticonvulsant activity at dosages of from 10 to 100 mg./kg. of body weight daily. The preferred compound 8-[1-methyl-4(4-fluorophenyl)butyl] gives 100% protection in mice against audiogenic seizures at dosages of 30 mg./kg. of body weight daily.

The compounds of this invention possess the unexpected properties of being active in the CNS areas only, and, specifically, as anticonvulsant agents. The corresponding 8-alkyl compounds possess both CNS and cardiovascular activities (See U.S. Pat. No. 3,493,579).

The compounds of this invention can be incorporated into pharmaceutical compositions suitable for oral, parenteral or rectal administration.

The compounds can be prepared for use by dissolving under sterile conditions, a salt form of the compounds in water (or an equivalent amount of non-toxic acid if the free base is used), or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol, or oil solutions or oil-water emulsions in the same manner as conventional medicinal substances are prepared.

The following examples further illustrate this invention without, however, limiting it thereto.

EXAMPLE 1

Preparation of
2-(3,5-dimethoxyphenyl)-5-(4-fluorophenyl)pentane

A solution of 77 g. of 3-(4-fluorophenyl)propylbromide in 300 ml. of ether was added dropwise over a 2 hour period to a refluxing solution of 10 g. of magnesium in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl)propylbromide was worked up in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-fluorophenyl)pentane, b.p. 145°–155°/0.05 mmHg.

Analysis Calcd. for $C_{19}H_{23}O_2F$: C, 75.60; H, 7.69.
Found: C, 75.87; H, 7.98.

EXAMPLE 2

Preparation of
2-(3,5-dihydroxyphenyl)-5-(4-fluorophenyl)pentane

Fifty grams of the above prepared 2-(3,5-dimethoxyphenyl)-5-(4-fluorophenyl)pentane, 450 ml. of acetic acid and 180 ml. of 48% HBr in water were mixed. While cooling, the mixture was saturated with hydrogen bromide gas (aproximately ½ hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(4-fluorophenyl)pentane as a brown oil which distills at 180°/0.01 mmHg.

Analysis Calcd. for $C_{17}H_{25}O_2F$: C, 74.20; H, 6.98.
Found: C, 73.56; H, 7.04.

EXAMPLE 3

1,4-Ethano-5-oxo-8-[1-methyl-4(4-fluorophenyl)-butyl]-10-hydroxy-1,2,3,4-tetrahydro-5H[1]benzopyrano[3,4-b]pyridine hydrochloride Ethyl 3-quinuclidinone-2-carboxylate hydrochloride (20.0 g.) was added in portions to 22.9 g. of 5-[(1-methyl-4-(4-fluorophenyl)butyl] rescorcinol in 37 ml. of methanesulfonic acid and 24 ml. of phosphorus oxychloride. The mixture was stirred at room temperature for 5 days. To the stirred mixture was added 20 ml. of chloroform and 200 ml. of water. The reaction mixture was stirred for 20 minutes whereupon three layers formed. The water layer was removed and the mixture extracted with more water. The middle layer was then removed and concentrated in vacuo. The addition of $CH_3CN$ produced a solid which was crystallized from tetrahydrofuran to yield 16.4 g. of the intermediate as a white solid, m.p. 271°–281° C., which produced one spot in thin layer chromatography.

Analysis Calcd. for $C_{25}H_{27}NO_3ClF$. C, 67.55; H, 6.14; N, 3.15;
Cl, 8.00.
Found: C, 67:63; H, 6.22; N, 3.10;
Cl, 7.98.

EXAMPLE 4

5,5-Dimethyl-10-hydroxy-1,4-ethano-8-[1-methyl-4-(4-fluorophenyl)butyl]-1,2,3,4-tetrahydro-5H[1]benzopyrano[3,4-b]pyridine hydrobromide 1,4-Ethano-5-oxo-8-[1-methyl-4(4-fluorophenyl)-butyl]-10-hydroxy-1,2,3,4-tetrahydro-5H[1]benzopyrano[3,4-b] pyridine hydrochloride (13 g.) was stirred with chloroform, water and potassium bicarbonate for 30 minutes. The chloroform layer was separated and evaporated in vacuo. The concentrate was taken up in benzene, concentrated to dryness, dissolved in 80 ml. of anisole and added to a solution of 100 ml. of 3 l molar $CH_3MgBr$ in ether and 100 ml. of anisole. The reaction was stirred under a nitrogen atmosphere at 37° C. for 18 hours. Water (60 ml.) was slowly added to the reaction mixture while cooling, followed by 80 ml. of 20% sulfuric acid. The anisole was removed by steam distillation, and the resulting solid was recrystallized from $CH_3CN$ to yield 10.7 g. of product, m.p. 284°–286° C.

Analysis Calcd. for $C_{27}H_{33}NFO_2Br$: C, 64.19; H, 6.63; N, 2.78.
Found: C, 64.00; H, 6.74; N, 2.82.

EXAMPLE 5

1,4-Ethano-8-(4-p-methylphenyl-1-methylbutyl)-10-hydroxy-5-oxo-1,2,3,4-tetrahydro-5H[1]benzopyrano[3,4-b]pyridine Following a procedure similar to that described in Example 4, 1,4-ethano-8-(4-p-methylphenyl-1-methylbutyl)-5-oxo-10-hydroxy-1,2,3,4-tetrahydro-5H[1]benzopyrano[3,4-b] pyridine is prepared by reacting 3-quinuclidinone-2-carboxylate with 5(4-p-methylphenyl-1-methylbutyl) resorcinol in the presence of methanesulfonic acid and phosphorus oxychloride.

EXAMPLE 6

5,5-Dimethyl-10-hydroxy-1,4-ethano-8-(4-p-methylphenyl-1-methylbutyl)-1,2,3,4-tetrahydro-5H[1]benzopyrano[3,4-b]pyridine 5,5-Dimethyl-10-hydroxy-1,4-ethano-8-(4-p-methylphenyl-1-methylbutyl)-1,2,3,4-tetrahydro-5H[1]benzopyrano [3,4-b]pyridine is prepared by following a procedure similar to that described in Example 5, by reacting 1,4-ethano-10-hydroxy-8-(4-p-methylphenyl-1-methylbutyl)-5-oxo-1,2,3,4-tetrahydro-5H[1]benzo-zopyrano[3,4-b]pyridine with methyl magnesium bromide in anisole.

EXAMPLE 7

5,5-Dimethyl-10-methoxy-1,4-ethano-8-[1-methyl-4(4-fluorophenyl)butyl]-1,2,3,4-tetrahydro-5H[1]benzopyrano [3,4-b]pyridine To a solution of 5.02 g. (0.01 mol.) of 5,5-dimethyl-1,4-ethano-10-hydroxy-8-[1-methyl-4-(4-fluorophenyl)butyl]-1,2,3,4-tetrahydro-5H[1]benzopyrano[3,4-b]pyridine hydrobromide (Example 4) in 25 ml. hexamethylphosphoramide was added 3.10 g. (0.025 mole) of a 45% aqueous solution of potassium hydroxide. After stirring 10 minutes at room temperature, 1.57 g. (0.011 mole) methyl iodide was added and the reaction mixture was stirred at room temperature overnight. The solution was then treated with 50 ml. water and 100 ml. ether. After stirring the ether layer was separated and extracted with water, dried over magnesium sulfate and concentrated to an oil. This was purified by column chromatography on Florisil using chloroform as an eluant to give 3.52 g. of desired product. 81% yield.

EXAMPLE 8

5,5-Dimethyl-10-acetoxy-1,4-ethano-8-[1-methyl-4-(4-fluorophenyl)butyl]-1,2,3,4-tetrahydro-5H[1]benzopyrano[3,4-b]pyridine 5.02 g. (0.01 mole) of 5,5-dimethyl-10-hydroxy-1,4-ethano-8-[1-methyl-4-(4-fluorophenyl)butyl]-1,2,3,4-tetrahydro-5H[1]benzopyrano[3,4-b]pyridine hydrobromide was converted to the base by stirring 1 hour with warm chloroform and saturated potassium bicarbonate water solution. The chloroform layer was concentrated and the residue was dissolved in 6 ml. pyridine. Acetic anhydride (1.6 g.) was added and the mixture stirred 1 hour at room temperature then for 1 hour on the steambath. The solvents were then removed on a rotary evaporator. 50 ml. cyclohexane was added and the mixture was again concentrated on a rotary evaporator. Then 50 ml. cyclohexane and 25 ml. potassium bicarbonate and water solution was added. After stirring 5 minutes the cyclohexane layer was removed, extracted with water, then dried over magnesium sulfate and concentrated to give 4.15 g. of a colorless oil as the desired product. 88% yield.

EXAMPLE 9

5,5-Dimethyl-10-(4-piperidino butyryloxy)1,4ethano-8-[1-methyl-4-(4-fluorophenyl)butyl]-1,2,3,4-tetrahydro-5H[1]benzopyrano[3,4-b]pyridine hydrochloride 5.02 g. (0.01 mole) of 5,5-dimethyl-10-hydroxy-1,4-ethano-8-[1-methyl-4-(4-fluorophenyl)butyl]-1,2,3,4-tetrahydro-5H[1]benzopyrano[3,4-b]pyridine hydrobromide (Example 4) was converted to the base as described in Example 8. This was dissolved in 100 ml. of dry dichloromethane. Then 2.16 g. (0.0105 mole) of 4-piperidino butyric acid hydrochloride [P. A. Cruickshank and J. C. Sheehan, J. Am. Chem. Soc. 83 2891 (1961)] and 2.26 g. dicyclohexyl-carbodiimide was added. The mixture was stirred at room temperature overnight. The dicyclohexylrea was filtered. The filtrate concentrated to 15 ml. and 15 ml. ether was added to give 5.51 g. of product as a crystalline solid. 90% yield.

EXAMPLE 10

5,5-Dimethyl-10-(4-morpholino butyryloxy)-1,4-ethano-8-[1-methyl-4-(4-fluorophenyl)butyl]-1,2,3,4-tetrahydro-5H[1]benzopyrano[3,4-b]pyridine hydrochloride Using the method described in Example 9, 5.02 g. of 5,5-dimethyl-10-hydroxy-1,4-ethano-8-[1-methyl-4-(4-fluorophenyl)butyl]-1,2,3,4-tetrahydro-5H[1]benzopyrano [3,4-b]pyridine hydrobromide and 2.19 g. of 4-morpholino butyric acid hydrochloride [P. A. Cruickshank and J. C. Sheehan, J. Am. Chem. Soc. 83 2891 (1961)] was converted into 5.15 g. of product as a crystalline solid. 84% yield.

EXAMPLE 11

Tablets weighing 200 mg. and having the following composition are prepared by standard tableting procedure:

| Ingredient | Mg. |
|---|---|
| 5,5-Dimethyl-10-hydroxy-1,4-ethano-8-[1 methyl-4-(4-fluorophenyl)butyl]-1,2,3,4-tetrahydro-5H[1]benzopyrano [3,4-b]pyridine | 100 |
| Starch | 94 |
| Colloidal silica | 5 |
| Magnesium stearate | 1 |

It will be understood by those skilled in the art that the above composition can contain any of the compounds of this invention.

The compounds of this invention can be formulated into various pharmaceutical dosage forms such as tablets, capsules, pills and the like, for immediate or sustained release, by combining the active compound with suitable pharmaceutically acceptable carriers or diluents according to methods well known in the art. Such dosage forms may additionally include excipients, binders, fillers, flavoring and sweetening agents and other therapeutically inert ingredients necessary in the formulation of the desired pharmaceutical preparation.

I claim:

1. A compound of the formula

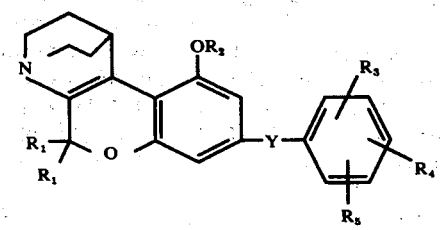

wherein each $R_1$ is loweralkyl; $R_2$ is hydrogen or loweralkyl; Y is a straight or branched chain alkylene group having from one to ten carbon atoms and each $R_3$, $R_4$ and $R_5$ are the same or different members of the group consisting of hydrogen, halo, trifluoromethyl, loweralkyl, or N,N-diloweralkylamino; and the pharmaceutically acceptable salts thereof.

2. A compound in accordance with claim 1 wherein $R_1$ is methyl.

3. A compound in accordance with claim 1, 5,5-dimethyl-10-hydroxy-1,4-ethano-8-[1-methyl-4-(4-fluorophenyl)butyl]-1,2,3,4-tetrahydro-5H[1]benzopyrano[3,4-b]pyridine or a pharmaceutically acceptable salt thereof.

4. A compound of the formula

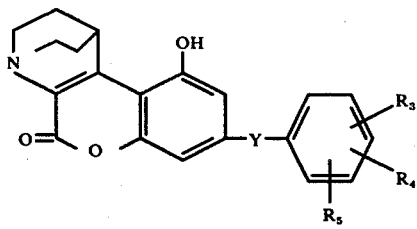

wherein Y is a straight or branched chain alkylene group having from one to 10 carbon atoms and each $R_3$, $R_4$, and $R_5$ are the same or different members of the group consisting of hydrogen, halo, trifluoromethyl or loweralkyl, and the pharmaceutically acceptable salts thereof.

* * * * *